(12) United States Patent
Valentino et al.

(10) Patent No.: US 12,371,716 B2
(45) Date of Patent: Jul. 29, 2025

(54) METHOD OF MANUFACTURING SUGAR CANE POLYVINYL ALCOHOL

(71) Applicants: Garrett Valentino, Scottsdale, AZ (US); George Liu, Scottsdale, AZ (US); James Reinertson, Rye, NH (US)

(72) Inventors: Garrett Valentino, Scottsdale, AZ (US); George Liu, Scottsdale, AZ (US); James Reinertson, Rye, NH (US)

(*) Notice: Subject to any disclaimer, the term of this patent is extended or adjusted under 35 U.S.C. 154(b) by 0 days.

(21) Appl. No.: 18/581,247

(22) Filed: Feb. 19, 2024

(65) Prior Publication Data

US 2024/0279689 A1    Aug. 22, 2024

Related U.S. Application Data

(60) Provisional application No. 63/485,684, filed on Feb. 17, 2023.

(51) Int. Cl.
| | | |
|---|---|---|
| *C12P 7/06* | (2006.01) | |
| *C07C 1/24* | (2006.01) | |
| *C07C 29/147* | (2006.01) | |
| *C07C 67/38* | (2006.01) | |
| *C08F 116/06* | (2006.01) | |
| *C08F 118/08* | (2006.01) | |
| *C13B 10/02* | (2011.01) | |

(52) U.S. Cl.
CPC ............. *C12P 7/06* (2013.01); *C07C 1/24* (2013.01); *C07C 29/147* (2013.01); *C07C 67/38* (2013.01); *C08F 116/06* (2013.01); *C08F 118/08* (2013.01); *C13B 10/02* (2013.01)

(58) Field of Classification Search
None
See application file for complete search history.

(56) References Cited

U.S. PATENT DOCUMENTS

| | | | | |
|---|---|---|---|---|
| 2012/0077247 A1* | 3/2012 | Medoff | ............ | A61P 31/04 435/183 |
| 2019/0032094 A1* | 1/2019 | Yu | ............ | C12P 7/10 |
| 2020/0354891 A1* | 11/2020 | Foody | ............ | D21C 3/06 |

FOREIGN PATENT DOCUMENTS

CN    109879996 A    *    6/2019

OTHER PUBLICATIONS

CN109879996A. Jun. 14, 2019, English language machine translation (Year: 2019).*
International Search Report of PCT/US2025/016387, dated Mar. 11, 2025.

* cited by examiner

*Primary Examiner* — Christian L Fronda
(74) *Attorney, Agent, or Firm* — POLSINELLI PC

(57) ABSTRACT

A method of manufacturing sugar cane polyvinyl alcohol wherein sugar cane bagasse is processed into polyvinyl alcohol. Processing raw materials including sugar cane bagasse and deionized water. Enzymatically hydrolyzing and using saccharification on the sugar cane bagasse to obtain sugar cane bagasse enzymatic hydrolysate. Fermenting the sugar cane bagasse solution. Distilling the fermented sugar cane bagasse solution to obtain ethanol solution and lignin solution. Transferring the distilled solutions to an ethylene plant area to obtain a polymer grade ethylene product. Transferring the polymer grade ethylene product to an acetic acid evaporator to generate vinyl acetate. Introducing the vinyl acetate into an autoclave with methanol solution wherein said solutions undergo a reflux reaction process. Ethyl acetate is then dissolved in methanol to prepare a polyvinyl acetate solution which undergoes alcoholysis wherein the product is then washed and deionized, yielding polyvinyl alcohol.

9 Claims, 10 Drawing Sheets

Fermentation
30

Collect the activated and expanded yeast in a centrifuge tube, centrifuge at 6000 rpm for 2 minutes, discard the supernatant, collect the bacteria, wash the bacteria with sterile water for 1 to 2 times, and add sterile deionized water Resuspend the bacteria, and inoculate it into the sterilized sugar cane bagasse enzymolysis solution according to the wet weight of the bacteria 5~8g/L, and use sodium hydroxide to adjust the pH of the solution to 5.0~5.5, and add iron sulfate and calcium carbonate at the same time Chelate and adsorb lignin and ferment for 36~60h; the yeasts are Candida Shekhata and Saccharomyces cerevisiae 1445.

31

Added masses of iron sulfate and calcium carbonate are respectively 10-20% and 15% of the volume of the sugar cane bagasse enzymatic hydrolysis solution.

Transferal to Ethylene Plant Area
50

The obtained ethanol is sent to the ethylene plant area and added with tetrafluorosilane and dodecyldimethyl tertiary amine modified γ-Al2O3 catalyst, dehydrated at 360~470°C to obtain crude ethylene, and then compressed, Alkaline washing, drying, rectification, and finally obtain polymer grade ethylene product.

51

Added mass of the γ-Al2O3 catalyst modified by tetrafluorosilane and dodecyldimethyl tertiary amine is 20-25% of the volume of ethanol.

52

Preparation method of the γ-Al2O3 catalyst modified by tetrafluorosilane and dodecyldimethyl tertiary amine is the hydrochloric acid reflux-oil column forming method, and the aluminum foil with a purity of 99.99% and the mass fraction are the 11% hydrochloric acid solution is mixed at the Al/Cl molar ratio of 1.6, stirred at a speed of 50r/min and slowly heated to 95°C. After the aluminum foil starts to dissolve, adjust the speed to 200r/min until the aluminum foil is completely dissolved, and then add 40% The methine tetraamine solution was reacted in a sealed tetrafluorosilane gas for 30 minutes, mixed evenly, and dropped into a 98°C oil column to form balls. After 4 hours, it was soaked in the dodecyl dimethyl tertiary amine solution for 1 to 2 hours, and then Move to an autoclave to age at 126°C for 17 hours, dry and roast to obtain modified alumina.

| Acetic Acid Evaporation |
| :---: |
| 60 |
| The prepared polymer-grade ethylene product is sent to the acetic acid evaporator and oxygen and acetic acid are introduced. After mixing, silica is used as the carrier, metal palladium, gold and potassium acetate are the active components at 120~200°C and 0.6~ Under 0.8Mpa conditions, the catalytic reaction generates vinyl acetate; the molar ratio of oxygen, ethylene, and acetic acid is 1:6:1; the catalytic component metal palladium, The content of gold and potassium acetate are 5~10g/L, 3~7g/L, 40~80g/L respectively. |
| 61 |

FIG. 7

Reflux Reaction
70

The prepared vinyl acetate is introduced into an autoclave, methanol solution is added, potassium persulfate solution with a volume fraction of 20% and 5M ferric sulfate solution are added as initiators, and dodecyl mercaptan is used as chain transfer agent. Under the protection of nitrogen, reflux reaction at 95~100°C for 1~4h to prepare polyvinyl acetate.

71

Added volume of methanol is 50-70% of the volume of vinyl acetate; the added mass of dodecyl mercaptan is 1~3% of the mass of vinyl acetate.

72

Volume of potassium persulfate solution added is 5-15% of the volume of vinyl acetate, and the volume of 5M ferric sulfate solution added is 20% of the volume of methanol.

| Alcoholysis |
| --- |
| 80 |
| Dissolve ethyl acetate in methanol to prepare a 15~25% polyvinyl acetate solution, add 10~20% volume fraction of sodium hydroxide solution at 40~45°C, alcoholysis for 2~4h.<br><br>81 |

FIG. 9

| Washing and Deionization |
| :---: |
| 90 |
| After the alcoholysis, the reaction product is washed with deionized water to neutrality and dried to obtain polyvinyl alcohol.<br><br>91 |

FIG. 10

METHOD OF MANUFACTURING SUGAR CANE POLYVINYL ALCOHOL

FIELD OF THE INVENTION

The present invention relates generally to a method of manufacturing polyvinyl alcohol. More specifically, the present invention is a method of manufacturing polyvinyl alcohol from sugar cane.

BACKGROUND OF THE INVENTION

Polyvinyl alcohol (PVA) is a water-soluble synthetic polymer. It is used in papermaking, textile warp sizing, a variety of coatings, and 3D printing. PVA is commonly supplied as colorless, odorless beads, or, as solutions in water.

Bio-based products mainly refer to lignocellulosic agricultural and forestry wastes such as straws other than grain, which are used as raw materials to produce environmentally friendly products. Producing environmentally friendly chemicals and green energy is the only way for mankind to achieve sustainable development. Bio-based chemical products and green energy issues have become the forefront of the world's scientific and technological fields.

Sugar cane bagasse is a major by-product of the sugar industry (approximately 24%-27%), mainly composed of cellulose, hemicellulose, lignin and pectin. The annual output of sugar cane bagasse in southern my country is about 20 million tons. Among them, about 90% of sugar cane bagasse is used in sugar mill boilers for power generation and steam supply, and about 10% is used in the production of animal feed such as cattle and sheep, production of fuel ethanol, papermaking and other fields, and the added output value is not high.

Polyvinyl alcohol is a kind of biodegradable high score widely used in medicine, health, food and chemical industry. The production routes of polyvinyl alcohol mainly include ethylene method and acetylene method. The ethylene method is based on ethylene and acetic acid. In the process of preparing polyvinyl alcohol from vinyl acetate, peroxygen is often used to obtain vinyl acetate products through catalytic oxidation and separation. Dibenzoyl or azobisisobutyronitrile is used as the initiator. In the reaction process, the butyronitrile or aldehyde initiator can produce highly toxic. As a by-product, the polyvinyl alcohol contains toxic impurities and restricts its application.

PVA within the field of prior art today are all made from fossil fuel natural gas. The present invention serves to introduce the world's first and only sugar cane PVA, through the form of PVA pellets, films, bags, fiber, and is blow moldable, extrusion moldable, and injection moldable. The present invention can replace many plastics of the world.

In view of the shortcomings of the prior art, the present invention discloses a method for preparing polyvinyl alcohol from sugar cane bagasse. The sugar cane bagasse is used as a raw material to prepare bioethanol through enzymatic saccharification and fermentation, and the ethanol is dehydrated to produce ethylene under the action of a catalyst. After compression, alkali washing, drying, and rectification, polymer grade ethylene is obtained; then polymer grade ethylene is used as a raw material to react with acetic acid to produce vinyl acetate. Potassium persulfate and dodecyl mercaptan are used as initiators and chain transfer respectively. Preparation to obtain polyvinyl acetate, after alcoholysis, washing, and drying, polyvinyl alcohol is finally obtained. The invention uses sugar cane bagasse as a raw material, improves the alcohol fermentation, ethylene preparation and vinyl acetate preparation processes, reduces the formation of other products, and increases the efficiency of the reaction.

SUMMARY OF THE INVENTION

A method of manufacturing sugar cane polyvinyl alcohol wherein sugar cane bagasse is processed into polyvinyl alcohol. The method includes the steps of raw material processing, enzymatic hydrolysis and saccharification, fermentation, distillation, transferal to a ethylene plant area, acetic acid evaporation, reflux reaction, alcoholysis, and washing and deionization.

BRIEF DESCRIPTION OF THE DRAWINGS

FIG. 4 is a diagram of the fermentation step of the present invention.

FIG. 6 is a diagram of the transferal to ethylene plant area step of the present invention.

FIG. 7 is a diagram of the acetic acid evaporation step of the present invention.

FIG. 8 is a diagram of the reflux reaction step of the present invention.

FIG. 9 is a diagram of the alcoholysis step of the present invention.

FIG. 10 is a diagram of the washing and deionization step of the present invention.

DETAIL DESCRIPTIONS OF THE INVENTION

Figure 1:
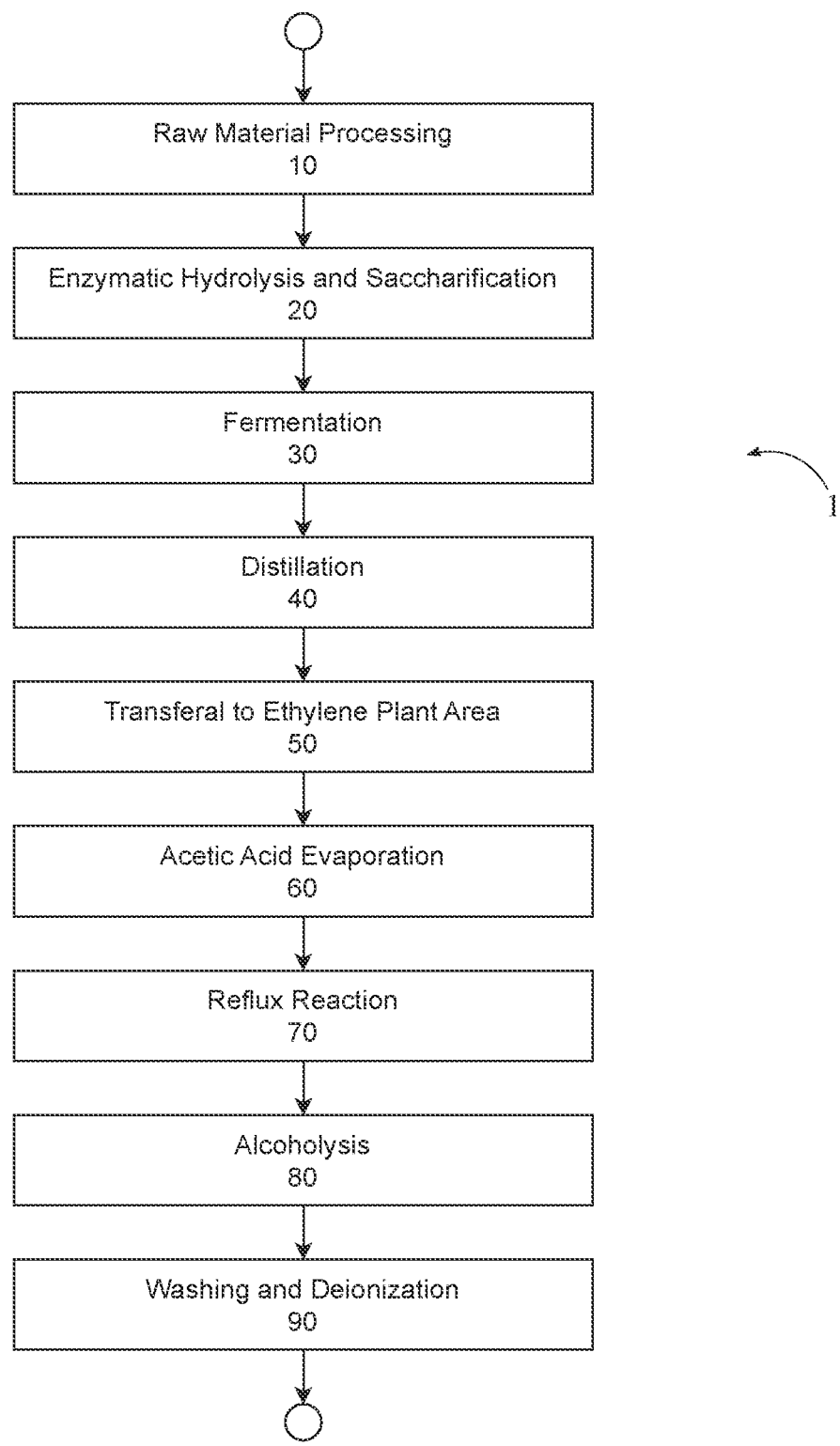
FIG. 1 is a flow diagram of the present invention.

All illustrations of the drawings are for the purpose of describing selected versions of the present invention and are not intended to limit the scope of the present invention.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification, and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate.

Within the context of the present invention, the term "solution," unless otherwise stated, refers to the mixture produced (i.e. the product) in the aforementioned process. For example, in a method comprising two steps the product of step one, would be referred to herein as the solution is step two. To further illustrate the point, the solution of step n will be the product of step n−1.

The present disclosure includes many aspects and features. Moreover, while many aspects and features relate to, and are described in the context of a method of manufacturing sugar cane polyvinyl alcohol, embodiments of the present disclosure are not limited to use only in this context.

As shown in FIG. 1, the present invention is a method of manufacturing sugar cane polyvinyl alcohol. In the preferred embodiment of the present invention, the method comprises as least one of the steps including: of raw material processing, enzymatic hydrolysis and saccharification, fermentation, distillation, transferal to a ethylene plant area, acetic acid evaporation, reflux reaction, alcoholysis, and washing and deionization. In the preferred embodiment of the present invention, the steps of the present invention comprise raw material processing, then enzymatic hydrolysis and saccharification, then fermentation, then distillation, then transferal to an ethylene plant area, then acetic acid evaporation then a reflux reaction, then alcoholysis, and lastly a washing and deionization step.

Figure 2:
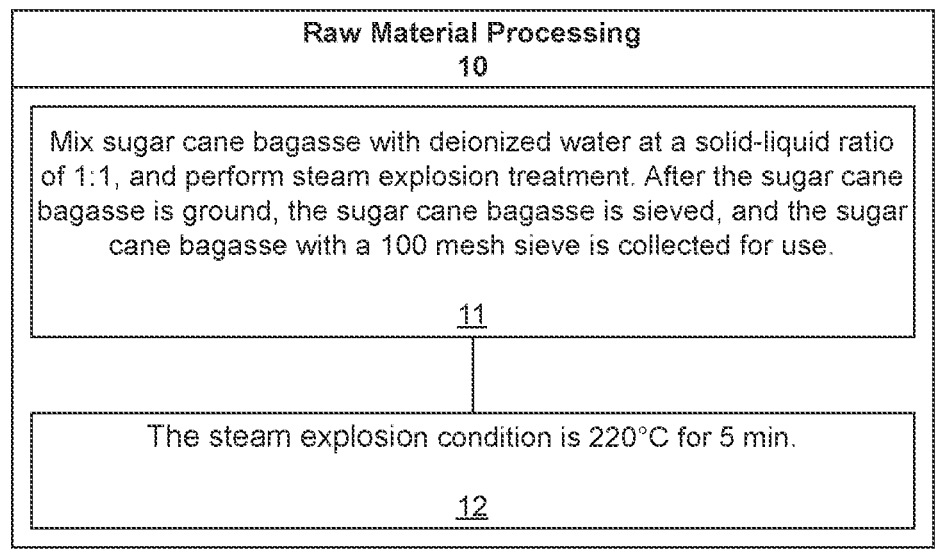
FIG. 2 is a diagram of the raw material processing step of the present invention.

As shown in FIG. 2, in the preferred embodiment of the present invention, within the step of raw material processing 10, sugar cane bagasse is combined 11 with deionized water at a solid to liquid ration of 1:1. Upon combination, the sugar cane bagasse and deionized water solution undergoes a steam explosion treatment. In the preferred embodiment of the present invention, the steam explosion condition 12 occurs at a temperature of 220° C. for a duration of five minutes. Additionally, the sugar can bagasse is ground and afterwards, the sugar cane bagasse is sieved. In the preferred embodiment of the present invention, the ground sugar cane bagasse is sieved using a 100 mesh sieve and collected.

Figure 3:
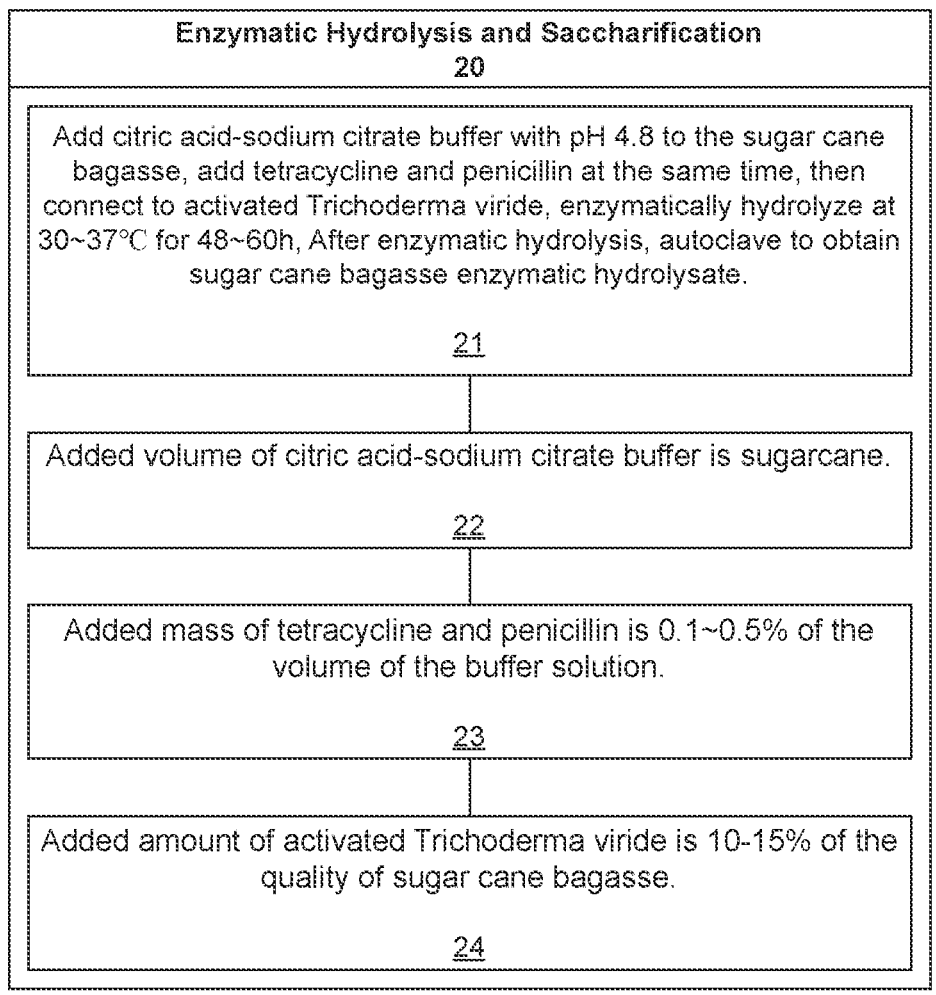
FIG. 3 is a diagram of the enzymatic hydrolysis and saccharification step of the present invention.
Figure 5:
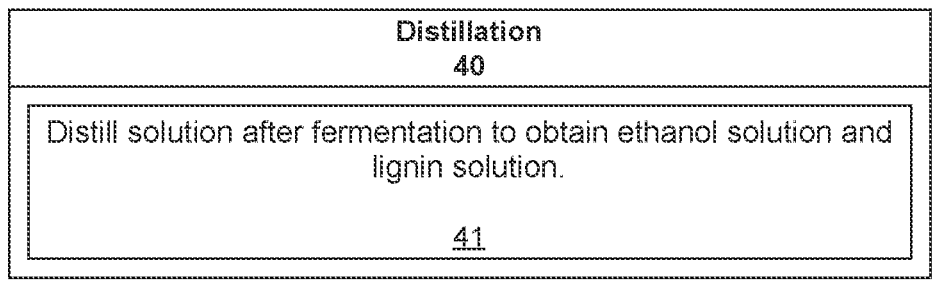
FIG. 5 is a diagram of the distillation step of the present invention.

Following the raw material processing 10 step of the present invention, the sugar cane bagasse undergoes an enzymatic hydrolysis and saccharification step 20, as shown in FIG. 3, wherein a volume of citric acid-sodium citrate buffer is added 21 to the collected sugar cane bagasse. In the preferred embodiment of the present invention, the buffer comprises a pH of 4.8. Furthermore, simultaneously, a mass of tetracycline and penicillin are added to the solution wherein "the solution" refers to the sugar cane bagasse and citric acid-sodium citrate buffer mixture. The solution is then connected to an amount of activated *Trichoderma viride* and enzymatically hydrolyzed. In the preferred embodiment of the present invention, enzymatic hydrolysis occurs at a temperature between 30° C. and 37° C. for a duration of time between 48 hours and 60 hours. After enzymatic hydrolysis, the solution is then autoclaved to obtain a sugar cane bagasse enzymatic hydrolysate. In the preferred embodiment of the present invention the volume of citric acid-sodium citrate buffer is sugarcane 22. Additionally, in the preferred embodiment of the present invention, the mass of tetracycline and penicillin is between 0.1% and 0.5% of the volume of buffer solution 23. Furthermore, the amount of activated *Trichoderma viride* is between 10% and 15% of the quantity of sugar cane bagasse 24.

As shown in FIG. 4, the fermentation process 30 comprises collecting 31 activated and expanded yeast in a centrifuge tube. In the preferred embodiment of the present invention the centrifuge tube rotates at 6000 rpm for two minutes. Upon collecting yeast, discard the supernatant and collect the bacteria. The bacteria is then washed with sterile water at least once. In the preferred embodiment of the present invention, the bacteria is washed either once or twice. Sterile deionized water is then added to the bacteria to resuspend the bacteria and is then inoculated into the sterilized sugar cane bagasse enzymolysis solution according to the wet weight of the bacteria. In the preferred embodiment of the present invention, the wet weight of the bacteria is between five and eight g/L. Sodium hydroxide is then used to adjust the pH of the solution to pH between 5.0 and 5.5. Simultaneously add a mass of iron sulfate and a mass of calcium carbonate at the instance of chelation and adsorption of lignin. The solution is then fermented for a duration of time between 36 hours and 60 hours. In the preferred embodiment of the present invention, the yeasts are *Candida* Shekhata and *Saccharomyces cerevisiae* 1445. Further, in the preferred embodiment of the present invention the mass of iron sulfate is between 10% and 20% of the volume of the sugar cane bagasse enzymatic hydrolysis solution 32. Likewise, in the preferred embodiment, the mass of calcium carbonate is 15% of the volume of the sugar cane bagasse enzymatic hydrolysis solution 32.

In the preferred embodiment of the present invention, following the fermentation process, the solution undergoes distillation 40. During distillation 40, the solution is distilled to obtain an ethanol solution and lignin solution 41.

As shown in FIG. 6, during the step of transferal to ethylene plant 50, the obtained ethanol is sent 51 to the ethylene plant area and added with tetraflourosilane and a mass of dodecyldimethyle tertiary amine modified γ-Al2O3 catalyst. The solution is then dehydrated to obtain crude ethylene. In the preferred embodiment of the present invention, the dehydration process occurs at a temperature between 360° C. and 470° C. The crude ethylene is then compressed, alkaline washed, dried, and rectified. After rectification, a polymer grade ethylene is obtained. In the preferred embodiment of the present invention, the mass of the γ-Al2O3 catalyst modified by tetrafluorosilane and dodecyldimethyl tertiary anime is between 20% and 25% of the volume of ethanol 52. The present invention further comprises a preparation method 53 of the γ-Al2O3 catalyst modified by tetrafluorosilane and dodecyldimethyl tertiary amine wherein the preparation method is a hydrochloric acid reflux-oil column forming method. In the preparation method, aluminum foil with a purity of 99.99% and a mass fraction of 11% hydrochloric acid solution is mixed at an Al/Cl molar ratio of 1.6. The mixture is then stirred at a speed of 50 r/min and slowly heated to 95° C. After the aluminum foil starts to dissolve, the speed is adjusted to 200 r/min until the aluminum foil is completely dissolved. Then, 40% methine tetraamine solution is added and reacts in a sealed tetrafluorosilane gas for 30 minutes. The solution is then mixed evenly, and dropped into a 98° C. oil column to form balls. After 4 hours, the balls are soaked in the dodecyl dimethyl tertiary amine solution for 1 to 2 hours, then moved to an autoclave at 126° C. for 17 hours. The product is then dried and roasted to obtain modified alumina.

During the acetic acid evaporation method 60, as shown in FIG. 7, the prepared polymer-grade ethylene product is sent 61 to the acetic evaporator wherein oxygen and acetic acid are introduced. The solution is then mixed whereby silica is used as a carrier and metal palladium, gold and potassium acetate are utilized as active components. In the preferred embodiment of the present invention, the solution is then exposed to conditions comprising a temperature between 120° C. and 200° C., and between 0.6 Mpa and 0.8 Mpa. The exposure to such conditions induces a catalytic reaction which yields vinyl acetate. In the preferred embodiment of the present invention, the molar ratio of oxygen, ethylene, and acetic acid is 1:6:1. Additionally, in the preferred embodiment of the present invention, the catalytic component metal palladium, gold, and potassium acetate are between 5 g/L and 10 g/L, between 3 g/L and 7 g/L, and between 40 g/L and 80 g/L, respectively.

During the reflux reaction 70 step of the present invention, as shown in FIG. 8, the prepared vinyl acetate is introduced 71 into an autoclave wherein methanol solution is added along with potassium persulfate solution and ferric sulfate solution. In the preferred embodiment of the present invention, the potassium persulfate solution comprises a volume fraction of 20% and the ferric sulfate solution is a 5M ferric sulfate solution, wherein said solutions act as initiators. Furthermore, dodecyl mercaptan is used as chain transfer agent within the solution. Under the protection of nitrogen, a reflux reaction occurs at, thus preparing polyvinyl acetate. In the preferred embodiment of the present invention, the conditions of the reflux reaction occur between a temperature of 95° C. and 100° C. for a duration of time between one hour and four hours. Additionally, within the preferred embodiment of the present invention, the added volume of methanol solution is between 50% and 70% of the volume of vinyl acetate and the mass of dodecyl mercaptan is between 1% and 3% of the mass of vinyl acetate 72. Furthermore, within the preferred embodiment of the present invention, the volume of potassium persulfate solution added is between 5% and 15% of the volume of vinyl acetate, and the volume of 5M ferric sulfate solution added is 20% of the volume of methanol 73.

As shown in FIG. 9, during the alcoholysis step 80 of the present invention, the ethyl acetate is dissolved 81 in methanol to prepare polyvinyl acetate solution. In the preferred embodiment of the present invention, the dissolution produces a 15% to 25% polyvinyl acetate solution. Next, a sodium hydroxide solution is added to the solution. In the preferred embodiment of the present invention, the sodium hydroxide solution is between 10% and 20% volume fraction at a temperature between 40° C. and 45° C. Further, in the preferred embodiment of the present invention, as shown in FIG. 9, the process of alcoholysis occurs for a duration of time between two and four hours.

Following alcoholysis 80, the reaction product is washed 91 with deionized water, in the washing and deionizing process 90, until the product reaches neutrality and is then dried to obtain polyvinyl alcohol 91.

Although the invention has been explained in relation to its preferred embodiment, it is to be understood that many other possible modifications and variations can be made without departing from the spirit and scope of the invention.

What is claimed is:
1. A method of manufacturing sugar cane polyvinyl alcohol comprising the steps:
processing raw materials including sugar cane bagasse and deionized water; wherein the sugar cane bagasse is mixed with the deionized water at a solid-liquid ratio of 1:1 to obtain a sugarcane bagasse solution;
adding citric acid-sodium citrate buffer with pH 4.8, a mass of tetracycline, penicillin and activated *Trichoderma viride* to the sugarcane bagasse solution; wherein the mass of tetracycline and penicillin is simultaneously to the sugar cane bagasse solution; wherein the mass of tetracycline and penicillin is between 0.1% and 0.5% of the volume of the buffer solution; wherein the amount of activated *Trichoderma viride* is 10% to 15% of the quantity of sugar cane bagasse solution;
enzymatically hydrolyzing at a temperature between 30° C. and 37° C. for between 48 hours and 60 hours and using saccharification on the sugar cane bagasse to obtain sugar cane bagasse enzymatic hydrolysate;
fermenting the sugar cane bagasse solution;

distilling the fermented sugar cane bagasse solution to obtain ethanol solution and lignin solution;

transferring the distilled solutions to an ethylene plant area to obtain a polymer grade ethylene product;

transferring the polymer grade ethylene product to an acetic acid evaporator to generate vinyl acetate;

introducing the vinyl acetate into an autoclave with methanol solution wherein said solutions undergo a reflux reaction process.

2. The method of manufacturing sugar cane polyvinyl alcohol of claim 1, further comprising the step of:

alcoholysis wherein ethyl acetate is dissolved in methanol to prepare a 15% to 25% polyvinyl acetate solution;

further adding sodium hydroxide solution; and the combined solution undergoing alcoholysis.

3. The method of manufacturing sugar cane polyvinyl alcohol of claim 2 further comprising the step of:

washing and deionizing the product of the alcoholysis process to obtain polyvinyl alcohol.

4. The method of manufacturing sugar cane polyvinyl alcohol of claim 1, wherein:

the sugar cane bagasse mixture undergoes a steam explosion treatment comprising steam explosion conditions of 220° C. for 5 minutes;

the sugar cane bagasse is ground;

the ground sugar cane bagasse is sieved through a 100 mesh sieve; and the sieved sugar cane bagasse is collected.

5. The method of manufacturing sugar cane polyvinyl alcohol of claim 1, wherein during the fermentation process:

activated and expanded yeast is collected in a centrifuge tube rotating at 6000 rpm for 2 minutes;

wherein the yeasts are *Candida* Shekhata and *Saccharomyces cerevisiae* 1445;

the supernatant of the centrifuged solution is discarded and bacteria is collected;

the collected bacteria is washed with sterile water at least once;

sterile deionized water is added to resuspend the bacteria;

the bacteria is inoculated into the sterilized sugar cane bagasse enzymolysis solution according to the wet weight of the bacteria;

sodium hydroxide is used to adjust the pH of the solution to a pH between 5.0 and 5.5;

iron sulfate and calcium carbonate are added at the moment of chelation and adsorption of lignin;

the solution is fermented for a duration between 36 hours and 60 hours.

6. The method of manufacturing sugar cane polyvinyl alcohol of claim 1, wherein during the transferring of the distilled solutions to an ethylene plant area:

the obtained ethanol is sent to the ethylene plant area and added with a mass of tetrafluorosilane and dodecyldimethyl tertiary amine modified $\gamma$-Al2O3 catalyst, wherein the mass of the $\gamma$-Al2O3 catalyst modified by tetrafluorosilane and dodecyldimethyl tertiary amine is between 20% and 25% of the volume of ethanol;

the solution is dehydrated at a temperature between 360° C. and 470° C. to obtain crude ethylene;

the crude ethylene undergoes a process to obtain a polymer grade ethylene product, said process comprising the steps of:

compression;

alkaline washing;

drying; and rectification.

7. The method of manufacturing sugar cane polyvinyl alcohol of claim 6, further comprising:

a preparation method of the $\gamma$-Al2O3 catalyst modified by tetrafluorosilane and dodecyldimethyl tertiary amine;

said preparation method is a hydrochloric acid reflux-oil column forming method.

8. The method of manufacturing sugar cane polyvinyl alcohol of claim 1, wherein upon the methanol solution being added into the autoclave with the vinyl acetate:

potassium persulfate solution with a volume fraction of 20% and 5M ferric sulfate solution are added as initiators, a mass of dodecyl mercaptan is added as a chain transfer agent;

under protection of nitrogen, the reflux reaction occurs at a temperature between 95° C. and 100° C. for a duration of time between one and four hours, thus producing polyvinyl acetate;

the added volume of methanol is between 50% and 70% of the volume of vinyl acetate; and the mass of dodecyl mercaptan is 1~3% of the mass of vinyl acetate.

9. The method of manufacturing sugar cane polyvinyl alcohol of claim 8, wherein the volume of potassium persulfate solution added is between 5% and 15% of the volume of vinyl acetate, and the volume of 5M ferric sulfate solution added is 20% of the volume of methanol.

* * * * *